United States Patent
Anderson et al.

(10) Patent No.: US 6,874,522 B2
(45) Date of Patent: Apr. 5, 2005

(54) LUER-ACTUATED SOLUTION PATH CONNECTOR WITH MEMBRANE AND CONTAINER USING THE CONNECTOR AND A METHOD FOR ESTABLISHING FLUID COMMUNICATION WITH THE CONTAINER

(75) Inventors: Keith M. K. Anderson, Libertyville, IL (US); Raf Castellanos, Roselle, IL (US); Bill Hurst, Burlington, WI (US); Michael T. K. Ling, Vernon Hills, IL (US); Dan Marcquenski, Lake Zurich, IL (US); Michael W. Scharf, McHenry, IL (US); Jennifer L. Masek, Lindenhurst, IL (US); Gregory Thomas Marn, Libertyville, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 245 days.

(21) Appl. No.: 10/173,890

(22) Filed: Jun. 18, 2002

(65) Prior Publication Data

US 2003/0230340 A1 Dec. 18, 2003

(51) Int. Cl.⁷ .......................... F16K 17/40; A61M 5/32
(52) U.S. Cl. ........................... 137/68.3; 285/3; 604/411; 604/415
(58) Field of Search .............................. 137/68.11, 68.3; 285/2, 3, 4; 604/244, 411, 415, 905

(56) References Cited

U.S. PATENT DOCUMENTS

| | | | |
|---|---|---|---|
| 3,202,442 A | * | 8/1965 | Abbey et al. ................... 285/3 |
| 3,285,627 A | * | 11/1966 | Kozulla et al. ................. 285/3 |
| 3,844,585 A | * | 10/1974 | Sands et al. .................... 285/3 |
| 4,022,205 A | | 5/1977 | Tenczar |
| 4,217,897 A | | 8/1980 | Sneider ....................... 604/204 |
| 4,331,146 A | * | 5/1982 | Brignola ...................... 604/200 |
| 4,636,204 A | | 1/1987 | Christopherson et al. ... 604/535 |
| 4,883,473 A | | 11/1989 | Thomas ....................... 604/217 |
| 4,886,497 A | | 12/1989 | Scholl, Jr. |
| 5,106,127 A | * | 4/1992 | Briet ............................. 285/4 |
| 5,176,415 A | | 1/1993 | Choksi et al. .............. 285/331 |
| 5,190,521 A | | 3/1993 | Hubbard et al. ............ 604/512 |
| 5,336,192 A | | 8/1994 | Palestrant .............. 604/167.04 |
| 5,501,676 A | | 3/1996 | Niedospial et al. ......... 604/534 |
| 5,554,130 A | | 9/1996 | McDonald et al. |
| 5,669,891 A | | 9/1997 | Vaillancourt ................ 604/537 |
| 5,772,625 A | | 6/1998 | Krueger et al. ................. 604/9 |

(Continued)

FOREIGN PATENT DOCUMENTS

| | | |
|---|---|---|
| EP | 0 157 224 A2 | 10/1985 |
| EP | 0 611 223 A1 | 8/1994 |
| EP | 0 830 874 A2 | 3/1998 |

*Primary Examiner*—John Rivell
(74) *Attorney, Agent, or Firm*—Jeffrey C. Nichols; Joseph P. Reagen; Bell, Boyd & Lloyd

(57) ABSTRACT

A connector, a container using the connector and a method for establishing fluid communication with a container. The connector may include a first coupling member and a second coupling member. The container may attach to the first coupling member. The first coupling member may have a first passageway with a spike and a membrane located therein. The second coupling member may have a second passageway. The first coupling member may engage the second coupling member and may further pierce the membrane with the spike. The first coupling member may further have a female end of a luer-lock, and the second coupling member may have a male end of a luer-lock. The first coupling member and the second coupling member may be engaged by twisting the male end and the female end of the coupling members to form the connector and establish fluid communication with the container.

21 Claims, 3 Drawing Sheets

U.S. PATENT DOCUMENTS

| | | | |
|---|---|---|---|
| 5,817,082 A | * 10/1998 | Niedospial et al. | 604/411 |
| 5,891,129 A | * 4/1999 | Daubert et al. | 604/411 |
| 5,895,383 A | 4/1999 | Niedospial, Jr. | 604/403 |
| 5,897,526 A | 4/1999 | Vaillancourt | 604/82 |
| 5,902,298 A | * 5/1999 | Niedospial et al. | 604/411 |
| 5,954,104 A | 9/1999 | Daubert et al. | 141/329 |
| 6,003,566 A | * 12/1999 | Thibault et al. | 604/416 |
| 6,070,623 A | * 6/2000 | Aneas | 604/200 |
| 6,171,287 B1 | 1/2001 | Lynn et al. | 604/256 |
| 6,189,580 B1 | 2/2001 | Thibault et al. | 141/25 |
| 6,382,442 B1 | * 5/2002 | Thibault et al. | 604/411 |
| 6,695,829 B2 | * 2/2004 | Hellstrom et al. | 604/415 |

* cited by examiner

LUER-ACTUATED SOLUTION PATH CONNECTOR WITH MEMBRANE AND CONTAINER USING THE CONNECTOR AND A METHOD FOR ESTABLISHING FLUID COMMUNICATION WITH THE CONTAINER

BACKGROUND OF THE INVENTION

The present invention generally relates to a connector, a container using the connector and a method for establishing fluid communication with the container. More specifically, the connector relates to a first coupling member and a second coupling member between a container and a patient. The container may be, for example, a flexible bag. The container may contain one or more medicaments, particularly for administration from the container to the patient.

Many pharmaceutical medicaments are delivered to hospitals or pharmacies in sealed containers, such as in flexible bags, glass or plastic vials, or glass or plastic bottles. Such containers often contain medicaments that are withdrawn from the container and administered to a patient during, for example, a kidney dialysis process. The containers typically receive a coupling member and a second coupling member. The coupling member is attached to or attaches to the container and directs the medicaments to the patient. The first coupling member and the second coupling member attach to form a passageway for the medicaments to flow to the patient.

The coupling member incorporates a stopper, or alternatively, a stopper is located in the container. The stopper prevents the solution from exiting the container. The coupling member often includes a needle that may pierce the stopper on the container. The piercing allows fluid to flow from the container, through the coupling member and to the patient.

Known connectors, however, fail to provide a mistake-proof connection between the coupling member and the stopper. A mistake-proof connection is needed in, for example, renal therapies, to insure that the correct medicaments are administered to a patient during such treatment. The needle associated with known coupling members permit pierce any stopper which may result in the wrong medicaments being administered to a patient.

A need, therefore, exists for a connector that may be mistake-proof. Moreover, a need exists for a container having such a connector. Finally, a need exists for a method for establishing fluid communication with the container.

SUMMARY OF THE INVENTION

The present invention relates to a connector, a container using the connector and a method for establishing fluid communication with the container. More specifically, the present invention relates to a connector and a container that retains fluid and provides an aseptic path upon engagement of the connector and a method for using the same.

To this end, in an embodiment of the present invention, a connector is provided. The connector has a first coupling member having a first passageway having a diameter and a membrane in the first passageway. A second coupling member is provided having a second passageway. Further, a spike may be provided in the first coupling member or the second coupling member wherein the spike has a third passageway. Connection of the first coupling member to the second coupling member penetrates the membrane of the first coupling member to provide fluid communication between the first passageway, the spike and the second passageway.

In an embodiment, the connector has a cap removably attached to the first coupling member.

In an embodiment, the connector has a cap removably attached to the second coupling member.

In an embodiment, the connector has a female connector on the first coupling member wherein the female end attaches to the second coupling member.

In an embodiment, the connector has a male connector on the second coupling member wherein the male end attaches to the first coupling member.

In an embodiment, the connector has a lip on the first coupling member wherein the lip has a diameter greater than a remainder of the first coupling member.

In an embodiment, the connector has a flange on the spike wherein the flange has a diameter greater than a remainder of the spike.

In an embodiment, the connector has a flange on the first coupling member wherein the flange has a diameter greater then a remainder of the first coupling member.

In an embodiment, the connector has a flange on the second coupling member wherein the flange has a diameter greater than a remainder of the second coupling member.

In another embodiment of the present invention, a container having walls defining an interior is provided. The container has a tube connected to one of the walls and extending outside of the interior of the walls. The container further has a first coupling member with a first passageway and a spike wherein the first coupling member connects to the tube and further wherein the spike is in the first passageway of the first coupling member. The container further has a second coupling member with a second passageway wherein the second coupling member attaches to the first coupling member to provide fluid communication with the interior.

In another embodiment of the present invention, the spike is located within the second coupling member instead of the first coupling member.

In an embodiment, the container has a membrane in the first passageway.

In an embodiment, the container has a female connecting end associated with the first coupling member.

In an embodiment, the container has a male connecting end associated with the second coupling member.

In an embodiment, the container has a cap enclosing the spike in the first passageway of the first coupling member.

In another embodiment of the present invention, a method for establishing fluid communication with a container having an interior wherein access to the container is provided by a port is provided. The method has the steps of: attaching a first coupling member to the container wherein the coupling member has walls defining a first passageway through the coupling member between a first end and a second end; sealing the first end of the coupling member with a membrane; inserting a spike in the passageway of the coupling member between the first end and the second end; and attaching a second coupling member at the second end of the first coupling member wherein attachment of the second coupling member causes the spike to pierce the membrane.

In an embodiment, the method provides the step of covering the first end of the first coupling member to enclose the first passageway and the spike in the first passageway.

In an embodiment of the present invention, an audible sound may be heard upon breaking of the membrane.

In an embodiment of the present invention, a reduction in the torque required to pierce the membrane may be felt when the membrane is ruptured.

In an embodiment, the method provides the step of securing the first coupling member to the second coupling member with a luer-lock.

In an embodiment, the method provides the step of forming a lip on the spike wherein the lip prevents the spike from exiting the first passageway.

In an embodiment, the method provides the step of aligning the first coupling member, the spike and the second coupling member to form a continuous passageway from the container.

In an embodiment, the method provides the step of removing a cap from the second coupling member prior to attaching the second coupling member to the first coupling member.

It is, therefore, an advantage of the present invention to provide a connector, a container using the connector and a method for establishing fluid communication with the container with a membrane located in a first connector.

Another advantage of the present invention is to provide a connector, a container using the connector and a method for establishing fluid communication with the container where a spike is located in the first connector.

A further advantage of the present invention is to provide a connector, a container using the connector and a method for establishing fluid communication with the container that utilizes a luer-lock type connector.

Moreover, an advantage of the present invention is to provide a connector, a container using the connector and a method for establishing fluid communication with the container that is mistake-proof.

A further advantage of the present invention is to provide a connector, a container using the connector and a method for establishing fluid communication with the container that provides access to medicaments.

Another advantage of the present invention is to provide a connector, a container using the connector and a method for establishing fluid communication with the container that does not require an exposed spike or an exposed needle.

Further, an advantage of the present invention is to provide a connector, a container using the connector and a method for establishing fluid communication with the container that provides an aseptic path for a solution.

A still further advantage of the present invention is to provide a connector, a container using the connector and a method for establishing fluid communication with the container that provides a connection that is leak-proof before, during and after the connection of a first coupling member to a second coupling member.

A further advantage of the present invention is to provide a connector, a container using the connector and a method for establishing fluid communication with the container wherein a user may sense the membrane being pierced while connecting the first coupling member and the second coupling member.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to a connector, a container using the connector and a method for establishing fluid communication with the container. The connector may be implemented to provide access and/or fluid communication with medicaments within a container. The connector is especially suitable for use with a container, such as a flexible bag. However, it will be appreciated that other applications of the present invention are feasible, including, but not limited to, applications using a vial or a bottle. The medicaments may be in liquid or solid form, such as, for example, a solution or suspension, or powdered or lyophilized, respectively.

The connector may include a first coupling member that may be attached to a container. Further, the connector may have a second coupling member that may be attached to a line that may direct the medicaments to a patient. A user may place the first coupling member and the second coupling member in a first position in which the first coupling member and the second coupling member are separate components. The user may secure the first coupling member to the second coupling member forming the connector and establishing fluid communication from the container through the connector.

Figure 1:
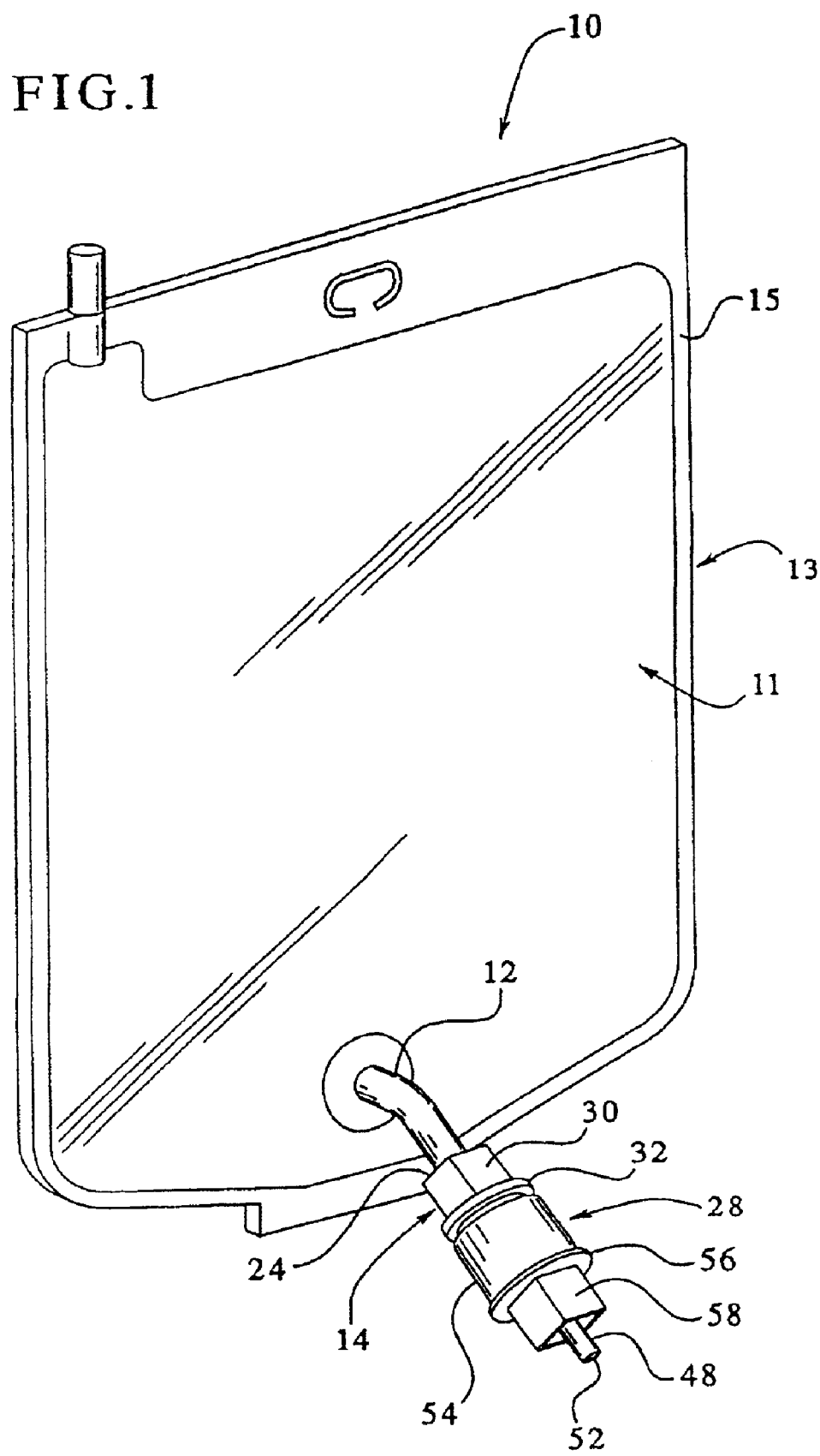
FIG. 1 illustrates a side-elevational view of an embodiment of the present invention showing a container implementing a connector of the present invention.

Referring now to the drawings, wherein like numerals refer to like parts, FIG. 1 illustrates a container 10 in the form of a bag or any other container, such as, a vial or a bottle. Preferably, the container 10 is a flexible bag having a first wall 11 and a second wall 13 that hold the medicaments in the container 10. The first wall 11 and the second wall 13 may be sealed around an edge 15 of the container 10. The container 10 may have a first tube 12 that may project from the container 10. The first tube 12 may provide fluid communication between the container 10 and a first coupling member 14.

The first coupling member 14 may have a first passageway 16 extending toward the container 10. The first passageway 16 may be attached to the first tube 12 to provide fluid communication between the container 10 and the first coupling member 14.

Figure 2:
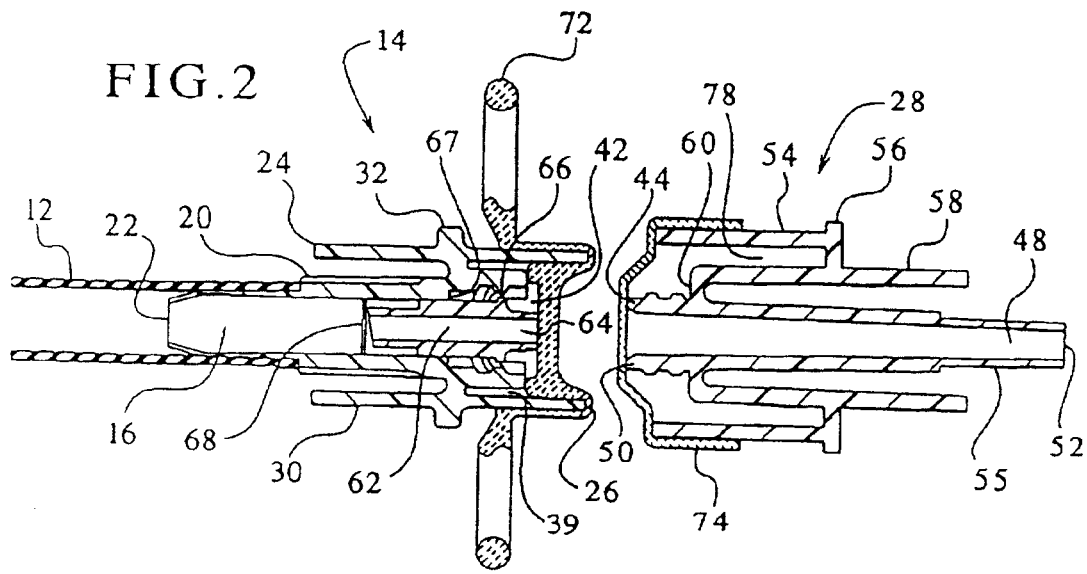
FIG. 2 illustrates a cross-sectional view of an embodiment of the present invention showing a first coupling member, a spike and a second coupling member in a first position.

FIG. 2 illustrates the first coupling member 14 and the second coupling member 28. Fluid communication between the container 10 and the patient is not established in FIG. 2 since the first coupling member 14 and the second coupling member 28 are not connected.

FIG. 2 further illustrates a diameter 20 of the first passageway 16. The diameter 20 may be tapered toward a distal end 22 of the first passageway 16 to form an interference fit between the diameter 20 and the first tube 12. The diameter 20 and the first tube 12 may further be attached using, for example, the heat generated by autoclave sterilization or an adhesive. The first coupling member 14 may have a first end 24 and a second end 26 defining a length of the first coupling member 14.

A second coupling member 28 may attach to the second end 26 of the first coupling member 14 to establish fluid communication between the first coupling member 14 and the second coupling member 28. Such fluid communication may be necessary for solution to flow from the container 10 through the first coupling member 14, a spike 62 and the second coupling member 28 to a patient in, for example, a dialysis process.

The first coupling member 14 may have a first section 30 that may be integrally formed with the diameter 20. The first section 30 may cover the first passageway 16. The first section 30 may be the outside surface of the first coupling member 14. The first section 30 may be constructed from any material such as, for example, plastic or rubber.

A flange 32 on the first coupling member 14 may provide the user with an area to grip on the first coupling member 14 for connecting the first coupling member 14 to the second coupling member 28. The first flange 32 may be integrally molded with the first section 30.

The second coupling member 28 may have a second section 54 that may be integrally formed with a second diameter 55 of the second passageway 48. The second section 54 may cover a portion of the second passageway 48. The second section 54 may be the outside surface of the second coupling member 28. The second section 54 may be constructed from any suitable material, such as, for example, plastic or rubber.

The second section 54 may have a flange 56 that may provide the user with an area to grip on the second coupling member 28. The flange 56 on the second coupling member 28 may be positioned at any point around the second section 54. Preferably, the flange 56 is centrally located around the second section 54. The second flange 56 may be integrally formed with the second section 54 and an internal section 58.

FIG. 2 also illustrates the first position wherein the first coupling member 14 and the second coupling member 28 are not connected to each other. The first coupling member 14 and the second coupling member 28 may be in the first position before a user connects the first coupling member 14 and the second coupling member 28. Fluid communication between the container 10 and the patient may not be established in the first position.

The first coupling member 14 may have a first gap 39 between the first section 30 and the diameter 20. The first gap 39 may be an area defined within the first section 30 and the diameter 20. The first gap 39 may provide an area for expansion for the first coupling member 14. The first coupling member 14 may expand outward from the first section 30 during connection of the second coupling member 28 if the male end 44 is slightly larger than the female end 42.

The female end 42 of a luer-lock type connector may be located at the second end 26 of the first coupling member 14. Additionally, a male end 44 of a luer-lock type connector may be located at a first end 50 of the second coupling member 28. The female end 42 may threadingly engage the male end 44 to establish fluid communication between the first coupling member 14, the spike 62 and the second coupling member 28. More specifically, engagement of the first coupling member 14 to the second coupling member 28 forces the spike 62 to pierce the membrane 68 located in the first passageway 16 of the first coupling member 14.

The first passageway 16 may be defined through the first coupling member 14 so the medicaments may flow through the first passageway 16 when the first coupling member 14 is connected to the second coupling member 28. The second passageway 48 may be defined through the second coupling member 28 so the medicaments may flow through the second passageway 48 when the first coupling member 14 is connected to the second coupling member 28. Of course, connection of the first coupling member 14 to the second coupling member 28 forces the spike 62 to pierce the membrane 68 in the first coupling member 14. After the membrane 68 is pierced, fluid communication with the container 10 is established through the first coupling member 14, the spike 62 and the second coupling member 28.

The internal section 58 of the second coupling member 28 may be attached to a second diameter 55 of the second passageway 48 at a junction 60. The junction 60 may be integrally formed with the internal section 58 of the second coupling member 28. The second coupling member 28 also has a second gap 78 that may be defined between the internal section 58 and the male end 44. The second gap 78 may provide a space for the second end 26 of the first coupling member 14 to slide into the second coupling member 28.

Referring to the first coupling member 14 in FIG. 2, the spike 62 may be located in the first passageway 16. In the alternative, the spike 62 may be located in the second passageway 48 of the second coupling member 28. Locating the spike 62 in the second passageway 48 of the second coupling member 28 instead of the first coupling member 14 may reduce surface contact of the spike 62 with the first passageway 16 and may, therefore, allow for effective steam sterilization of the spike 62, the first coupling member 14 and the second coupling member 28. Locating the spike 62 in the second passageway 48 of the second coupling member 28 may also eliminate the need for gamma sterilization. Although the figures and detailed description of the present invention illustrate the spike 62 located within the first coupling member 14 of the connector, it should be understood that the spike 62 may also be located in the second coupling member 28. Preferably, the spike 62 is hollow so that solution may flow through the spike 62 when the first coupling member 14 and the second coupling member 28 are connected. The spike 62 may have a base 64 that may be abutted by the male end 44 while connecting the first coupling member 14 and the second coupling member 28. The spike 62 may pierce the membrane 68 by twisting the first coupling member 14 and the second coupling member 28.

The membrane 68 may prevent medicaments from exiting the container 10 through the first passageway 16 of the first coupling member 14. The membrane 68 may prevent fluid or other solution or medicaments from exiting the container 10 through the first passageway 16 of the first coupling member 14 until the spike 62 pierces the membrane 68. In an embodiment, the membrane 68 may have a score line (not shown) that may allow the spike 62 to pierce the membrane 68. To this end, the score line may act as a target to which the spike 62 is directed and piercing of the membrane 68 may be effected accurately and precisely. The membrane 68 may be made any from suitable material, such as, for example, rubber or cellophane.

A flange 66 on the spike 62 may prevent the spike 62 from entering the first passageway 16. The spike 62 may slide into the first passageway 16 to pierce the membrane 68. The membrane 68 may prevent leaking of the medicaments from the container 10 prior to establishing fluid communication. After the membrane 68 is pierced by the spike 62, fluid communication may be established from the container 10, through the first coupling member 14 and the spike 62 and through the second coupling member 28. The flange 66 on the spike 62 may be located around an outer diameter of the spike 62 and may be integrally formed with the spike 62.

A lip 67 between the distal end 22 and the female end 42 may prevent the spike 62 from entering the first passageway 16. The lip 67 may be integrally formed with the inner diameter 18 and may protrude from the inner diameter 18. The lip 67 may prohibit the passage of the spike 62 over the lip 67 through the flange 66 on the spike 62. The lip 67 may be a distance from the female end 42 such that the spike 62 may slidably pierce the membrane 68 without entering the first passageway 16.

FIG. 2 further illustrates a first cap 72 and a second cap 74 that may prevent objects from making contact with the second end 26 of the first coupling member 14 and the first end 50 of the second coupling member 28, respectively. The first cap 72 and the second cap 74 may further preserve the sterility of the second end 26 of the first coupling member 14 and the first end 50 of the second coupling member 28, respectively. The first cap 72 and the second cap 74 may be constructed from any suitable material, such as, for example, plastic.

The first cap 72 may be removed from the first coupling member 14 prior to connecting the first coupling member 14 and the second coupling member 28. Likewise, the second cap 74 may be removed from the second coupling member 28 prior to connecting the second coupling member 28 to the first coupling member 14.

Figure 3:
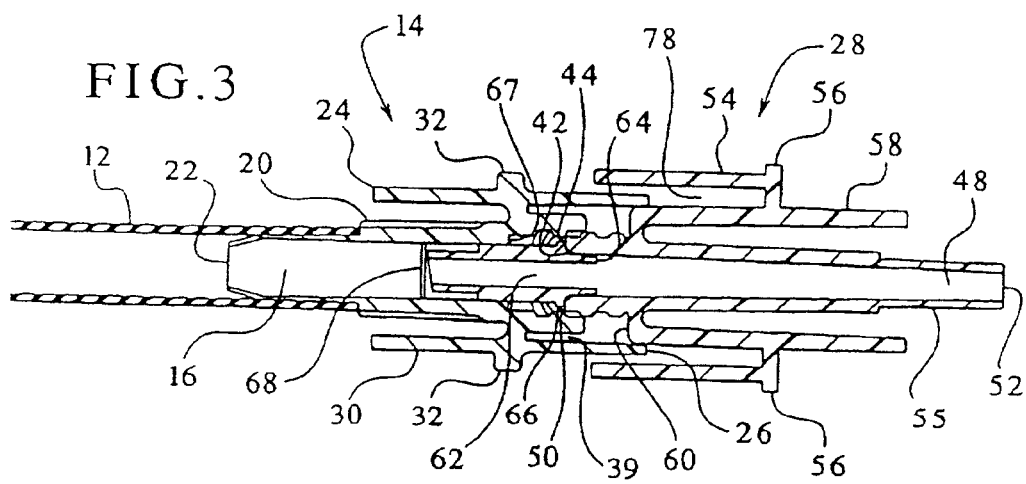
FIG. 3 illustrates a cross-sectional view of an embodiment of the present invention showing the first coupling member, the spike and the second coupling member in a second position.

FIG. 3 illustrates the first coupling member 14 and the second coupling member 28 wherein a user may abut the female end 42 and the male end 44. To this end, as shown in FIG. 3, a user may guide the second end 26 of the first coupling member 14 into the second coupling member 28. The second end 26 of the first coupling member 14 may slide into the second gap 78 of the first end 50 of the second coupling member 28. The second end 26 may slide into the second gap 78 so that alignment of the first coupling member 14 and the second coupling member 28 is not askew prior to connection and piercing of the membrane 68 following attachment of the first coupling member 14 to the second coupling member 28.

Figure 4:
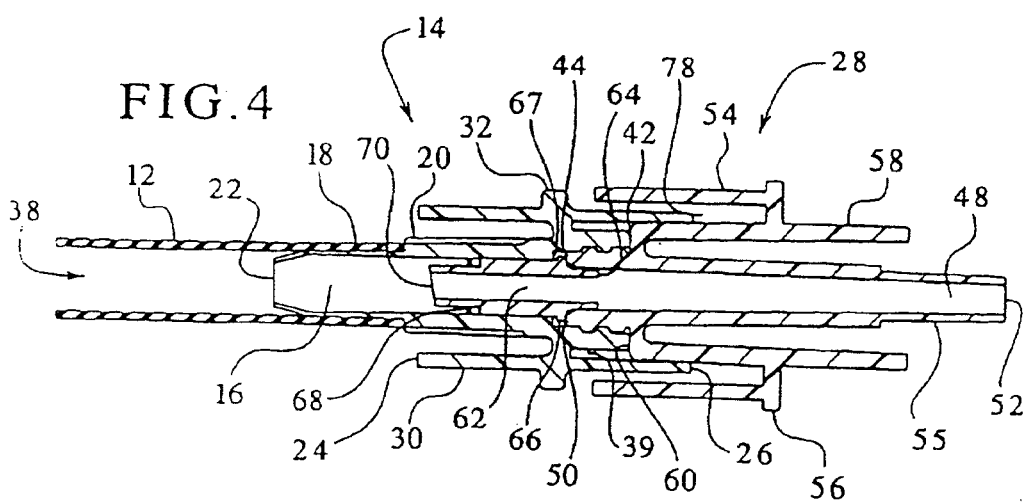
FIG. 4 illustrates a cross-sectional view of an embodiment of the present invention showing the first coupling member, the spike and the second coupling member in a third position.

FIG. 4 illustrates a position wherein the first coupling member 14, the spike 62 and the second coupling member 28 are connected. Fluid communication from the container 10 through the first coupling member 14, the spike 62 and the second coupling member 28 may be established when a user "twists" the first coupling member 14 and the second coupling member 28. Twisting the first coupling member 14 to connect to the second coupling member 28, allows engagement and may connect the female end 42 of the first coupling member 14 to the male end 44 of the second coupling member 28. The female end 42 and the male end 44 may engage using a luer-lock connection. Fluid communication from the container 10 through the first coupling member 14, the spike 62 and the second coupling member 28 may be established in the position shown in FIG. 4.

Connecting of the first coupling member 14 with the second coupling member 28 may produce a physical and/or audible confirmation that the membrane 68 has been pierced and/or that fluid communication may be established. More specifically, an audible "pop" may be heard when the pressure of the spike 62 is great enough to rupture the membrane 68. Additionally, once the membrane 68 is pierced, the torque required to push the spike 62 into the membrane 68 is reduced, creating a physical confirmation that the membrane 68 has been pierced. The physical and/or audible confirmation may aid patients who suffer from, for example, poor vision or other disabilities associated with, for example, renal disease.

The medicaments may pass through the first coupling member 14, the spike 62 and the second coupling member 28 through the first passageway 16 and the second passageway 48. After the spike 62 pierces the membrane 68, the first passageway 16 and the second passageway 48 may establish fluid communication from the container 10 through the first coupling member 14, the spike 62 and the second coupling member 28. The first passageway 16 and the second passageway 48 may extend from the distal end 22 of the first coupling member 14 to a second end 52 of the second coupling member 28.

Connecting the first coupling member 14 to the second coupling member 28 may cause the spike 62 to pierce the membrane 68 with a tip 70 of the spike 62. To pierce the membrane 68, the base 64 of the spike 62 may be advanced toward the membrane 68 by the male end 44. The tip 70 may pierce the membrane 68 after the base 64 of the spike 62 is advanced toward the membrane 68 by the male end 44. In an embodiment as previously set forth, the membrane 68 may have a score line that may simplify piercing of the membrane 68. After the tip 70 pierces the membrane 68, fluid communication from the container 10, through the first coupling member 14, the spike 62 and the second coupling member 28 to a patient may be established.

Figure 5:
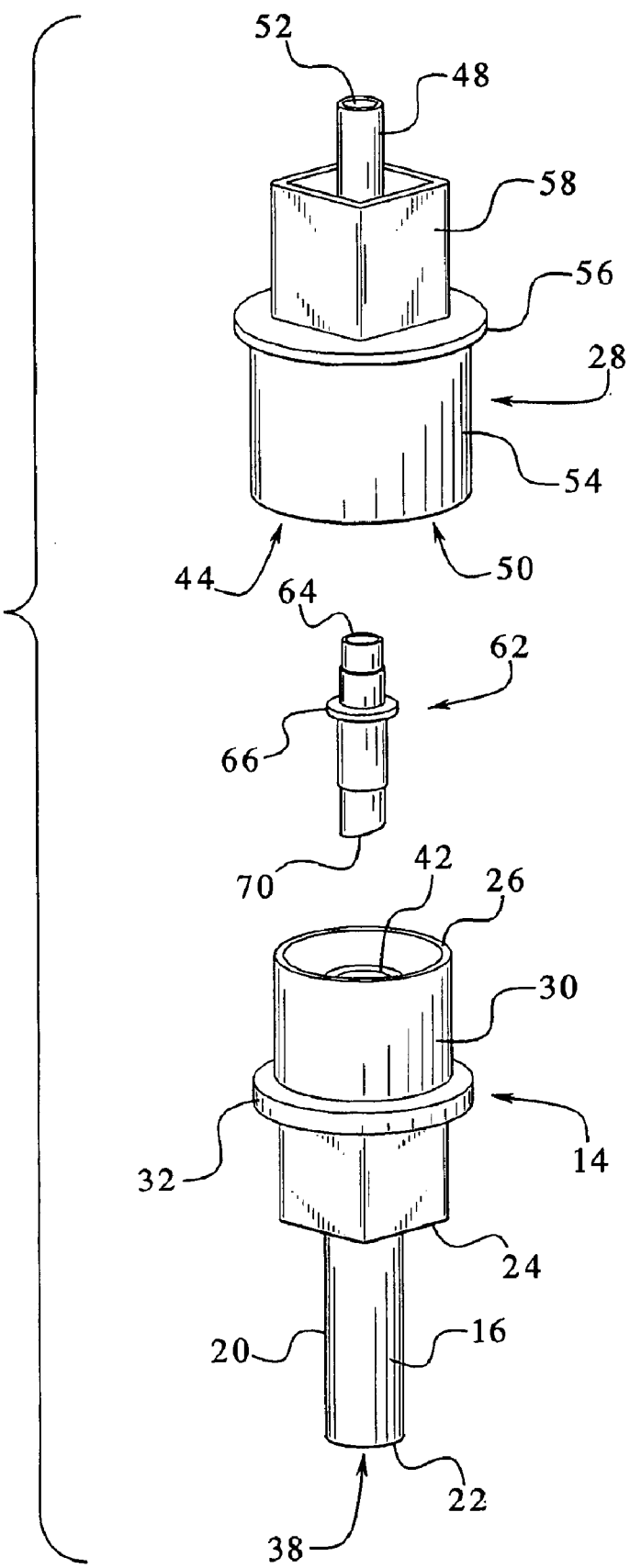
FIG. 5 illustrates an exploded perspective view of an embodiment of the present invention showing the first coupling member, the spike and the second coupling member.

FIG. 5 illustrates the first coupling member 14, the spike 62 and the second coupling member 28. The spike 62 may be inserted into the first coupling member 14 though the female end 42. In this manner, the spike 62 may pierce the membrane 68 when the first coupling member 14 and the second coupling member 28 are connected.

Connection of the female end 42 and the male end 44 advances the spike 62 through the first passageway 16 to pierce the membrane 68. Connecting the first coupling member 14 and the second coupling member 28 causes the first end 50 of the second coupling member 28 to force the base 64 toward the membrane 68. As the base 64 advances toward the membrane 68, the tip 70 may pierce the membrane 68, which may form the passageway 38 through the first coupling member 14 and the second coupling member 28. The flange 66 on the spike 62 may prevent the spike 62 from advancing beyond the lip 67 and into the first tube 12.

As a result of the construction and geometry of the connector, a mistake-proof connection may be established. Namely, a user may readily identify when the first coupling member 14 is connected to the second coupling member 28. Likewise, a user may know when the first coupling member 14 is not connected to the second coupling member 28. Further, a user may identify when the first coupling member 14 and the second coupling member 28 are connected. Namely, the construction of the connector allows a user to identify if the first coupling member 14 and the second coupling member 28 are connected to establish fluid communication. Moreover, a user may "feel" the piercing of the membrane 68 during connection of the first coupling member 14 and the second coupling member 28.

In use, a user may connect the first coupling member 14 to the second coupling member 28 to establish fluid communication from the container 10 to a patient. Fluid communication may be established from the container 10, through the first coupling member 14, the spike 62 and the second coupling member 28, to the patient following connection as a result of the membrane 68 in the first coupling member 14 being pierced by the spike 62 also in the first coupling member 14.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims.

We claim:

1. A connector comprising:
    a first coupling member having a first passageway with a diameter and further having a membrane in the first passageway;
    a second coupling member having a second passageway;
    a spike associated with the first coupling member wherein the spike has a third passageway and further wherein connection of the first coupling member to the second coupling member causes the spike to penetrate the membrane of the first coupling member to provide fluid communication between the first passageway, the spike and the second passageway; and
    a flange on the spike wherein the flange has a diameter greater than a remainder of the spike.

2. The connector of claim 1 further comprising:
    a cap removably attached to the first coupling member.

3. The connector of claim 1 further comprising:
    a cap removably attached to the second coupling member.

4. The connector of claim 1 further comprising:
    a female connector on the first coupling member wherein the female end attaches to the second coupling member.

5. The connector of claim 1 further comprising:
    a male connector on the second coupling member wherein the male end attaches to the first coupling member.

6. The connector of claim 1 further comprising:
    a lip on the first coupling member wherein the lip has a diameter greater than a remainder of the first coupling member.

7. The connector of claim 1 further comprising:
    a flange on the first coupling member wherein the flange has a diameter greater then a remainder of the first coupling member.

8. The connector of claim 1 further comprising:
    a flange on the second coupling member wherein the flange has a diameter greater than a remainder of the second coupling member.

9. The connector of claim 1 wherein the spike is located in the second coupling member.

10. A container having walls defining an interior, the container comprising:
    a tube connected to one of the walls and extending outside of the interior of the walls;
    a first coupling member having a first passageway and a spike that includes a flange having a diameter greater than a remainder of the spike, wherein the first coupling member connects to the tube and further wherein the spike is in the first passageway of the first coupling member; and
    a second coupling member having a second passageway wherein the second coupling member attaches to the first coupling member to provide fluid communication with the interior.

11. The container of claim 10 further comprising:
    a membrane in the first passageway.

12. The container of claim 10 further comprising:
    a female connecting end associated with the first coupling member.

13. The container of claim 10 further comprising:
    a male connecting end associated with the second coupling member.

14. The container of claim 10 further comprising:
    a cap enclosing the spike in the first passageway of the first coupling member.

15. A method for establishing fluid communication with a container having an interior wherein access to the container is provided by a port, the method comprising the steps of:
    attaching a first coupling member to the container wherein the coupling member has walls defining a first passageway through the coupling member between a first end and a second end;
    sealing the first end of the coupling member with a membrane;
    inserting a spike having a lip in the passageway of the coupling member between the first end and the second end;
    wherein the lip prevents the spike from exiting the first passageway; and
    attaching a second coupling member at the second end of the first coupling member wherein attachment of the second coupling member causes the spike to pierce the membrane.

16. The method of claim 15 further comprising the step of:
    covering the first end of the first coupling member to enclose the first passageway and the spike in the first passageway.

17. The method of claim 15 further comprising the step of:
    securing the first coupling member to the second coupling member with a luer-lock.

18. The method of claim 15 comprising the step of:
    aligning the first coupling member, the spike and the second coupling member to form a continuous passageway from the container.

19. The method of claim 15 further comprising the step of:
    removing a cap from the second coupling member prior to attaching the second coupling member to the first coupling member.

20. The method of claim 15 further comprising:
    producing an audible sound upon piercing of the membrane.

21. The method of claim 15 comprising:
    reducing an amount of torque required to force the spike into the membrane is felt upon piercing of the membrane.

* * * * *